US008668906B2

(12) United States Patent
Cuñé Castellana

(10) Patent No.: US 8,668,906 B2
(45) Date of Patent: Mar. 11, 2014

(54) LACTOBACILLUS PLANTARUM STRAINS AS HYPOCHOLESTEROLEMIC AGENTS

(75) Inventor: Jordi Cuñé Castellana, Bellaterra (ES)

(73) Assignee: Ab-Biotics S.A., Cerdanyola del Valles (ES)

( * ) Notice: Subject to any disclaimer, the term of this patent is extended or adjusted under 35 U.S.C. 154(b) by 0 days.

(21) Appl. No.: 13/500,799

(22) PCT Filed: Sep. 28, 2010

(86) PCT No.: PCT/EP2010/064304
§ 371 (c)(1),
(2), (4) Date: Apr. 6, 2012

(87) PCT Pub. No.: WO2011/042333
PCT Pub. Date: Apr. 14, 2011

(65) Prior Publication Data
US 2012/0213753 A1    Aug. 23, 2012

Related U.S. Application Data

(60) Provisional application No. 61/265,095, filed on Nov. 30, 2009.

(30) Foreign Application Priority Data

Oct. 9, 2009    (EP) .................................... 09172613

(51) Int. Cl.
*A01N 63/00* (2006.01)
(52) U.S. Cl.
USPC ...................................................... 424/93.45
(58) Field of Classification Search
None
See application file for complete search history.

(56) References Cited

FOREIGN PATENT DOCUMENTS

WO    WO 2006/025643    3/2006
WO    WO 2009/068474    * 6/2009

OTHER PUBLICATIONS

Nguyen et al., Characterization of *Lactobacillus plantarum* PH04, a potential probiotic bacterium with cholesterol-lowering effects, International Journal of Food Microbiology 113 (2007) 358-361.*
Bukowska et al., "Decrease in fibrinogen and LDL-cholesterol levels upon supplementation of diet with *Lactobacillus plantarum* in subjects with moderately elevated cholesterol". Atherosclerosis 1998, vol. 137, p. 437-438.
Cole et al., "The Ribosomal Database Project (RDP-II): introducing myRDP space and quality controlled public data" Nucl. Acids Res. 2007, vol. 35, p. 169-172.
Goldstein et al., "Statins, plant sterol absorption, and increased coronary risk". Journal of Clinical Lipidology, 2008, vol. 2, p. 304-305.
Kailasapathy "Microencapsulation of Probiotic Bacteria: Technology and Potential Applications". Curr Issues Intest Microbiol 2002, vol. 3, p. 39-48.
Lim et al., "Isolation of cholesterol lowering lactic acid bacteria from human intestine for probiotic use". J Vet Sci 2004, vol. 5, p. 391-395.
Naruszewicz et al., "Potential parapharmaceuticals in the traditional Polish diet". Journal of Physiology and Pharmacology 2005, vol. 56, suppl 1, p. 69-78.
NCBI Reference Sequences, downloaded from: www.ncbi.nlm.nih.gov/RefSeq/, Sep. 11, 2009, 3 pgs.
Plana et al., "Plant sterol-enriched fermented milk enhances the attainment of LDL-cholesterol goal in hypercholesterolemic subjects", Eur J Nutr., 2008, vol. 47, p. 32-39.
Ribosomal Database Project Release 10, downloaded from: www.rdp.cme.msu.edu/, Feb. 9, 2009, 1 pg.
Rodas et al., "Polyphasic study of wine *Lactobacillus* strains: taxonomic implications", Int J Syst Evol Microbiol 2005, vol. 55, p. 197-207.
Sánchez et al., "Polyphasic study of the genetic diversity of lactobacilli associated with 'Almagro' eggplants spontaneous fermentation, based on combined numerical analysis of randomly amplified polymorphic DNA and pulsed-field gel electrophoresis patterns", Journal of Applied Microbiology 2004, vol. 97, p. 446-458.
Tanaka et al., "Screening of Lactic Acid Bacteria for Bile Salt Hydrolase Activity". Journal of Dairy Science 1999, vol. 82, p. 2530-2535.
Tenover et al., "Interpreting chromosomal DNA restriction patterns produced by pulsed-field gel electrophoresis: criteria for bacterial strain typing" J Clin Microbiol 1995, vol. 33, p. 2233-2239.
Wang et al., "Naive Bayesian Classifier for Rapid Assignment of rRNA Sequences into the New Bacterial Taxonomy". Appl. Environ. Microbiol 2007, vol. 73, p. 5261-5267.
Wong et al., "Colonic health: fermentation and short chain fatty acids". J Clin Gastroenterol 2006, vol. 40, p. 235-243.
Zhou et al., "Acute oral toxicity and bacterial translocation studies on potentially probiotic strains of lactic acid bacteria", Food Chem Toxicol 2000, vol. 38, p. 153-161.
European Food Safety Authority, "Gudiandce on the Assessment of Bacterial Susceptibility to Antimicrobials of Human and Veterinary Importance," EFSA Journal 2012; 10(6):2740, pp. 1-10.

* cited by examiner

*Primary Examiner* — Suzanne M Noakes
*Assistant Examiner* — Stephen Chong
(74) *Attorney, Agent, or Firm* — Squire Sanders (US) LLP

(57) ABSTRACT

The invention relates to a composition comprising an effective amount of at least one of the strains selected from the group consisting of *Lactobacillus plantarum* CECT 7527, *Lactobacillus plantarum* CECT 7528, and *Lactobacillus plantarum* CECT 7529, These new strains have good probiotic features and are useful for the prevention and/or the treatment of cardiovascular disorders.

16 Claims, 1 Drawing Sheet

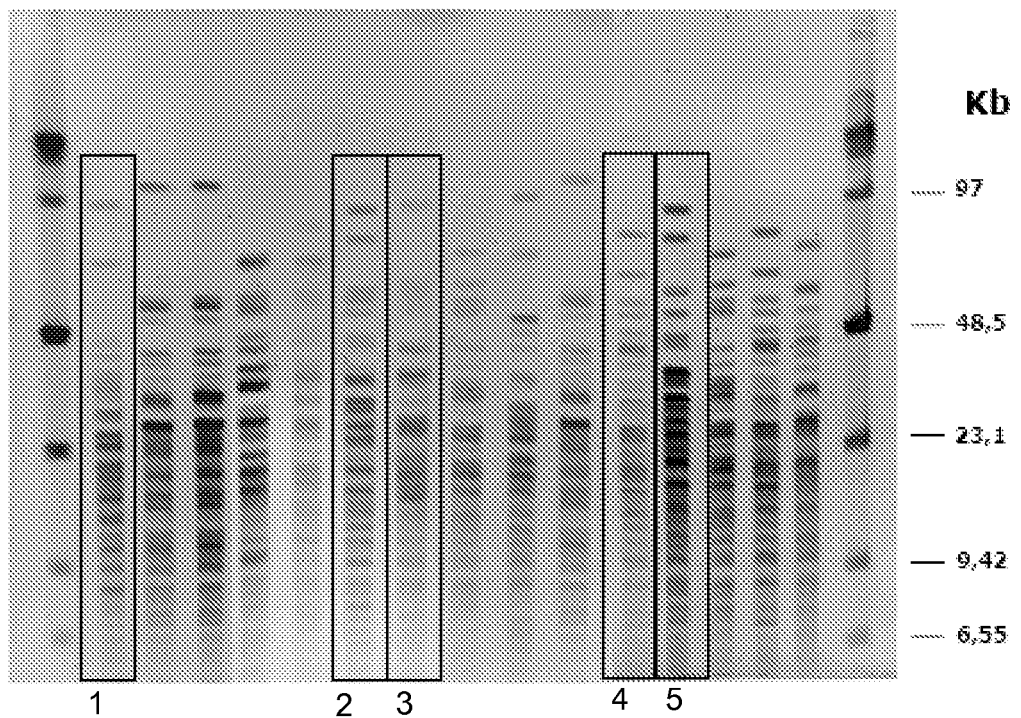
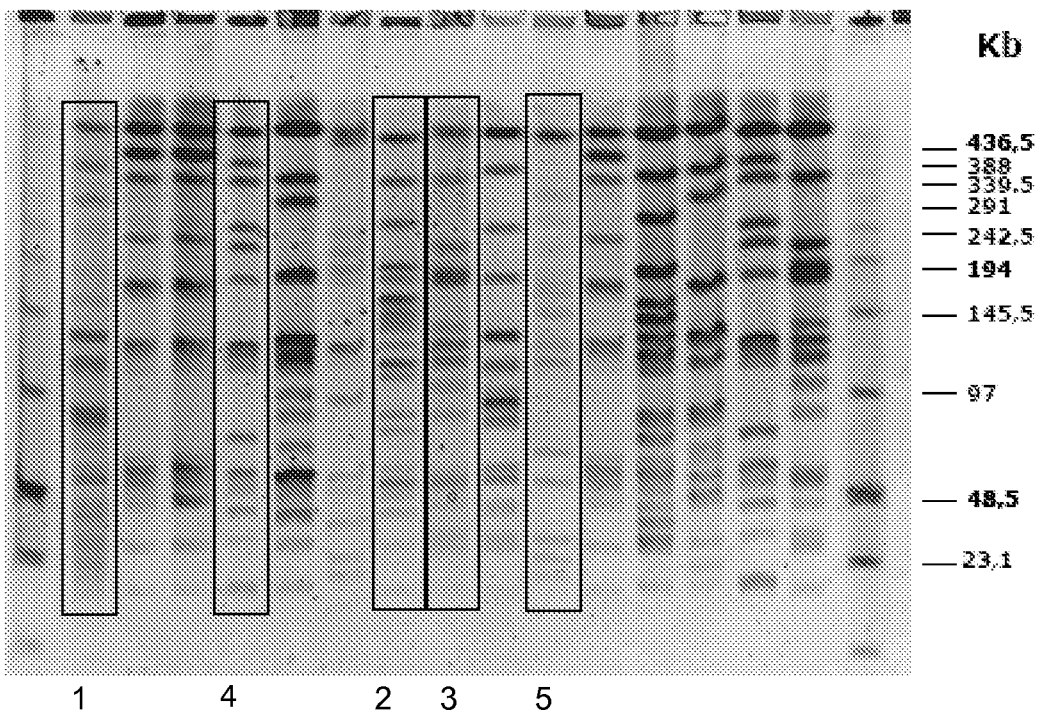

SEQUENCE LISTING

```
<160> NUMBER OF SEQ ID NOS: 6

<210> SEQ ID NO 1
<211> LENGTH: 19
<212> TYPE: DNA
<213> ORGANISM: artificial sequence
<220> FEATURE:
<223> OTHER INFORMATION: forward Eub27f primer

<400> SEQUENCE: 1
gagtttgatc ctggctcag                                              19

<210> SEQ ID NO 2
<211> LENGTH: 22
<212> TYPE: DNA
<213> ORGANISM: artificial sequence
<220> FEATURE:
<223> OTHER INFORMATION: reverse Eub1492r primer

<400> SEQUENCE: 2
tacggytacc ttgttacgac tt                                          22

<210> SEQ ID NO 3
<211> LENGTH: 20
<212> TYPE: DNA
<213> ORGANISM: artificial sequence
<220> FEATURE:
<223> OTHER INFORMATION: forward 27f primer

<400> SEQUENCE: 3
agagtttgat cctggctcag                                             20

<210> SEQ ID NO 4
<211> LENGTH: 57
<212> TYPE: DNA
<213> ORGANISM: artificial sequence
<220> FEATURE:
<223> OTHER INFORMATION: forward 357f primer
```

```
<400> SEQUENCE: 4
cgcccgccgc gccccgcgcc cggcccgccg cccccgcccc cctacgggag gcagcag       57

<210> SEQ ID NO 5
<211> LENGTH: 20
<212> TYPE: DNA
<213> ORGANISM: artificial sequence
<220> FEATURE:
<223> OTHER INFORMATION: reverse 907r primer

<400> SEQUENCE: 5
ccgtcaattc ctttgagttt                                                 20

<210> SEQ ID NO 6
<211> LENGTH: 19
<212> TYPE: DNA
<213> ORGANISM: artificial sequence
<220> FEATURE:
<223> OTHER INFORMATION: reverse 1492r primer

<400> SEQUENCE: 6
ggttaccttg ttacgactt                                                  19
```

LACTOBACILLUS PLANTARUM STRAINS AS HYPOCHOLESTEROLEMIC AGENTS

This application claims the benefit of European Patent Application 09172613.3 filed on 9 Oct. 2009 and U.S. Provisional Patent Application Ser. No 61/265,095 filed on 30 Nov. 2009.

FIELD OF THE INVENTION

The present invention relates to the fields of medicine, microbiology and nutrition and particularly, to novel probiotic strains of *Lactobacillus plantarum* for use in the reduction of cholesterol.

BACKGROUND ART

Abnormally high cholesterol levels (hypercholesterolemia) are strongly associated with cardiovascular disease because they promote atheroma development in arteries.

Potential hypocholesterolemic pharmaceuticals and food products are continuously being developed in order to control serum cholesterol in persons with abnormally high levels. These pharmaceuticals can be based on interruption of the enterohepatic circulation (EHC) of bile salts. Bile salt metabolism and cholesterol metabolism are closely linked. Bile salts are the water-soluble excretory end-products of cholesterol, and are essential for emulsification of fats in the digestive tract. They are synthesised in the liver mainly as glyco- or tauro-conjugates. Bile salts are secreted several times a day (six on average) in the duodenum, and pass through the jejunum into the ileum. During intestinal transit, most of the bile salts are reabsorbed to return to the liver via the portal vein. A small proportion is lost within the faeces and this loss is to be newly synthesised from endogenous cholesterol in the liver. An increase of the amount of bile salts that are lost within the faeces results in an increased neosynthesis of cholesterol, thus effectively reducing the endogenous cholesterol pool. A group of currently used hypocholesterolemic drugs named resins (Cholestyramine, Colestipol, Colesevelam) are active through this mechanism of action.

Apart from the pharmaceutical or surgical attempts to lower serum cholesterol levels through interruption of the EHC, it has been suggested that the ingestion of certain bacterial cells might also influence cholesterol levels. Intestinal bacteria can influence cholesterol levels through assimilation of exogenous cholesterol from the diet in the bacterial membrane or through bile salt deconjugation. During intestinal transit, bile salts undergo a number of bacterial transformations of which one of the most important is bile salt deconjugation. The ability to deconjugate (or hydrolyse) bile salts is encountered in some intestinal lactic acid bacteria (LAB) species, but also in other genera. Upon bile salt deconjugation, glycine or taurine is liberated from the steroid moiety of the molecule, resulting in the formation of free (deconjugated) bile salts. Free bile salts are more easily precipitated at low pH. They are also less efficiently reabsorbed than their conjugated counterparts. Hence, deconjugated bile salts are more readily excreted within the faeces that conjugated bile salts. Bile salt deconjugation influences the EHC by increasing the excretion of bile salts and is believed to be much more effective in the reduction of blood cholesterol levels than the mere retention of exogenous cholesterol.

Bile salt hydrolase (BSH), the enzyme responsible for bile salt deconjugation during EHC, has been detected in several LAB species indigenous to the gastrointestinal tract. Tanaka et al. (cf. "Screening of Lactic Acid Bacteria for Bile Salt Hydrolase Activity", *Journal of Dairy Science* 1999, vol. 82, p. 2530-35) screened more than 300 strains of LAB from the genera *Bifidobacterium* and *Lactobacillus* and the species *Lactococcus lactis, Leuconostoc mesenteroides*, and *Streptococcus thermophilus*. Results obtained for 273 strains showed that BSH activity is heterogeneously distributed among the different species. According to this study, nearly all bifidobacterial strains have BSH activity, whereas this activity can only be found in selected strains of lactobacilli.

*Lactobacillus plantarum* is a Gram-positive aerotolerant LAB commonly found in many fermented food products as well as anaerobic plant matter. It is also present in saliva (from which it was first isolated). *L. plantarum* strains are especially suitable for the industrial preparation of fermented food products thanks to their good survival rate through the industrial process and conservation period, as well as their high acidification profile and good organoleptic properties. Some strains of *L. plantarum* are also considered as probiotics. Probiotics are live microorganisms which, when administered in adequate amounts, confer a health benefit on the host. To be termed as probiotic, the bacteria must fulfil several requirements related to their lack of toxicity, viability in reaching the lower gastrointestinal tract (GIT) and adhesion to the intestinal mucosa, among others. Most probiotic bacteria belong the LAB group but, nevertheless, it is generally known that probiotic features and benefits are extremely strain-dependent, even among LAB of the same species.

The commercial *L. plantarum* 299v strain is generally regarded as probiotic and has been described to decrease the fibrinogen and cholesterol levels in serum when ingested in the form of a probiotic drink (cf. Bukowska et al., "Decrease in fibrinogen and LDL-cholesterol levels upon supplementation of diet with *Lactobacillus plantarum* in subjects with moderately elevated cholesterol" *Atherosclerosis* 1998, vol. 137, p. 437-38). However, LDL-cholesterol reduction was very moderate in these studies and was accompanied by a similar mild reduction of HDL-cholesterol. No data related to BSHA of *L. plantarum* 299v has been published.

It is therefore desirable to provide new improved probiotic strains to be used as hypocholesterolemic agents.

SUMMARY OF THE INVENTION

The present invention provides new improved probiotic strains for the reduction of blood cholesterol and, consequently, for the prevention and treatment of cardiovascular disorders.

Three new probiotic *Lactobacillus plantarum* strains isolated from human faeces are provided by the present inventors. The strains were found to have surprisingly high BSH activity. As mentioned above, the close relationship existing between high bacterial BSH activity and the reduction of cholesterol renders the present strains useful as hypocholesterolemic agents. The working examples below demonstrate that these strains have significantly higher BSH activity as compared to relevant, commercially available *L. plantarum* strains, such as *L. plantarum* 299v or the *L. plantarum* strain that is present in the commercial probiotic-mixture VSL#3. It is also shown that the strains of the invention are effective in the reduction of culture cholesterol from soluble cholesterol containing media. Even though each of the new strains on their own demonstrates advantages with respect to known strains, these advantages are magnified when the three strains are used together, thus showing a synergic behaviour.

The cholesterol-lowering activity of the strains of the invention has also been demonstrated in vivo. The example below demonstrates that a product containing the probiotic strains of the invention is particularly effective in the reduction of cholesterol in when administered to hypercholesterolemic subjects.

Accordingly, a first aspect of the invention relates to a composition comprising an effective amount of at least one of the strains selected from the group consisting of *Lactobacillus plantarum* CECT 7527, *Lactobacillus plantarum* CECT 7528, and *Lactobacillus plantarum* CECT 7529, or mutant strains thereof, wherein the mutant strains are obtained by using the deposited strains as starter material, and wherein the mutant strains retain or further improve the cholesterol lowering activity of the parent strains. In a particular embodiment, the invention relates to a composition comprising an effective amount of at least one of the strains selected from the group consisting of *Lactobacillus plantarum* CECT 7527, *Lactobacillus plantarum* CECT 7528, and *Lactobacillus plantarum* CECT 7529.

The term "effective amount" as used herein, means an amount of an active agent high enough to deliver the desired benefit, but low enough to avoid serious side effects within the scope of medical judgment.

Another embodiment of the present invention relates to a composition comprising an effective amount of *Lactobacillus plantarum* CECT 7527, *L. plantarum* CECT 7528, and *L. plantarum* CECT 7529 or mutant strains thereof, wherein the mutant strains are obtained by using the deposited strains as starter material, and wherein the mutant strains retain or further improve the cholesterol lowering activity of the parent strains. In a particular embodiment, the composition of the invention comprises an effective amount of *Lactobacillus plantarum* CECT 7527, *L. plantarum* CECT 7528, and *L. plantarum* CECT 7529.

It is clear that by using the deposited strains as starting material, the skilled person in the art can routinely, by conventional mutagenesis or re-isolation techniques, obtain further mutants or derivatives thereof that retain the herein described relevant features and advantages. Accordingly, the term "a mutant thereof" relates to mutant strains obtained by using the deposited strains as starting material, said mutant strains retaining or enhancing the cholesterol lowering properties of the parent strains. The skilled person in the art will decide upon the adequate method to be employed for determining the cholesterol lowering activity of the strains. Examples of possible methods to measure this activity are shown in the examples bellow.

The strains of this invention have the advantage that they are particularly useful as probiotics. As mentioned above, probiotic bacteria must fulfil several requirements related to lack of toxicity, viability, adhesion and beneficial effects. These probiotic features are strain-dependent, even among bacteria of the same species. Therefore, it is important to find those strains that have a better performance in all probiotic requirements. The examples below demonstrate that the present strains have excellent probiotic features.

The strains of the invention have demonstrated that they are highly resistant to the conditions of the gastrointestinal environment of mammals (acidic environment, high lysozyme, bile salt and oxygen peroxide concentrations), thus being able to survive passage through the GIT. The strains also have good adhesion to the intestinal epithelium, which allows them to remain in the intestinal tract and to exert their probiotic effects. When compared with other commercial strains, the strains of the invention show a better resistance to GIT conditions and higher adhesion capability. Additionally, they have also demonstrated to be safe, since they have no toxic effects, they do not lead to an increase in translocation of LAB, nor facilitate enterobacterial translocation in host mammals.

Further, the present strains have several beneficial effects in the host. In addition to their cholesterol lowering activity, they benefit the intestinal microbiota balance due to their antagonistic activity. The term "antagonistic activity" refers to the inhibition of growth of gastrointestinal non-beneficial bacteria by the activity of probiotic bacteria. The condition of having inadequate gastrointestinal microbial balance is known as disbiosis and has multiple negative consequences for human well-being. It will be shown below that the strains have a higher capacity to inhibit the growth of pathogenic strains when compared to other commercial *L. plantarum* strains.

The strains also produce large quantities of short chain fatty acids (SCFA). Production of SCFA from non-digestible fibres is an interesting probiotic ability. This ability is desirable in a probiotic because the produced SCFA show several beneficial properties in the host (cf. Wong J., "Colonic health: fermentation and short chain fatty acids", *J Clin Gastroenterol* 2006, vol. 40, p. 235-43). Among SCFA, propionic and butyric acid production are of greater interest for the scope of the present invention. The first has an anti-inflammatory effect, useful in order to reduce the systemic inflammation. The global inflammation has an incidence in the atherogenesis, which is one of the most important cardiovascular risk factors (cf. Naruszewicz M., "Potential parapharmaceuticals in the traditional Polish diet" 2005, *Journal of Physiology and Pharmacology*, vol. 56, suppl 1, p. 69-78). Butyric acid is generally known to be beneficial for colonic epithelium, since it is the main energy source for colonic cells.

In exerting several beneficial effects in the human host, these probiotic bacteria are useful as therapeutic or prophylactic agents. Particularly, the strains of the present invention are effective in reducing blood cholesterol levels. As explained above, high cholesterol levels are strongly associated with cardiovascular disease because they promote atheroma development in arteries. Thus, the strains of the invention are useful for the prevention or treatment of cardiovascular disorders.

Accordingly, another aspect of the invention is related to a composition comprising an effective amount of at least one of the strains of this invention, or mutant strains thereof, for use as a prevention and/or therapeutic agent. In a preferred embodiment, the composition of the invention is for use in the prevention or treatment of cardiovascular disorders in an animal, including a human. In another preferred embodiment the invention provides the use of the composition as described above for the manufacture of a medicament for the prevention and/or treatment of cardiovascular disorders. This may be alternatively formulated as a method for the prevention and/or treatment of cardiovascular disorders in an animal, including a human, comprising administering to said animal in need thereof an effective amount of the composition of the invention.

In another embodiment, the composition of the invention is used as a hypocholesterolemic agent. In a further embodiment, the invention provides the use of the composition as described above for the manufacture of a medicament for the reduction of cholesterol. This may be alternatively formulated as a method for the reduction of cholesterol in an animal, including a human, comprising administering to said animal in need thereof an effective amount of the composition of the invention.

The composition of the invention can be administered to healthy subjects as well as to patients that suffer form a coronary disorder. In a particular embodiment the subject receiving the composition of the invention suffers from hypercholesterolemia.

The probiotic compositions of the invention have the further advantage of lacking the side effects presented by plant sterols, which have been described to be contraindicated in combination with statin in sterol hyperabsorbant subjects. Recent evidence suggests that some of the residual coronary risk seen with statin monotherapy is a consequence of statins actually increasing coronary risk in patients who are hyperabsorbers of sterols, including plant sterols. Sterol hyperabsorbent subjects amount to around 25% of the population and most of them have been shown to contain polymorphisms in the adenosine-5'-triphosphate (ATP) binding cassette (ABC) half-transporter ABCG8 (Goldstein M et al, "Statins, plant sterol absorption, and increased coronary risk". *Journal of Clinical Lipidology*, 2008, vol. 2, p. 304-305). Furthermore, it has been suggested that the effects of dietary plant sterol enrichment and statin therapy are additive in elevating blood and tissue plant sterol levels, and that this is particularly evident in sterol hyperabsorbers. The probiotic composition of the invention does not have these drawbacks and can be administered to any population and in combination with statins or any other cholesterol-lowering drug.

Thus, in a particular embodiment, the composition of the invention is administered to sterol hyperabsorbent subjects. In another particular embodiment, the composition of the invention is administered in combination with a statin.

The strains of the invention also promote immunomodulatory effects in the host, since they induce an improved cytokine pattern from the intestinal mucosa. This immunomodulatory effects are beneficial to the host because they help achieve an improved disease resistance and diminished risk of allergies. It is known that Gram negative bacteria living in the GIT show the molecule LPS (lipopolysaccharide) on their cell surface, which induces the production of inflammatory markers from the intestinal mucosa cells. Probiotic supplementation can change this situation to favour one greater presence of Gram positive bacteria in the GIT (grouped in the lactic acid bacteria group), with better ecologic fitness or with antagonistic properties against some Gram negative microorganisms, thus reducing the presence of LPS in the intestinal mucosa. Nevertheless, some probiotic microorganisms show the ability to modulate per se the production of cytokines, which are messenger molecules that regulate the inflammatory and immune responses in the body. Particularly, some probiotic bacteria induce a better balanced pattern between pro/anti-inflammatory signalling in the intestinal mucosa (without reducing the number of Gram negative bacteria). As mentioned above, this bacterially stimulated immunomodulation also has an anti-atherosclerotic effect.

As will be illustrated below, it was found that the strains of the invention promote per se a reduction of the inflammatory tumor necrosis factor-α (TNF-α) levels and an increase of the anti-inflammatory interleukin-10 (IL-10) levels produced by intestinal mucosa cells, thus inducing an improved cytokine pattern from the intestinal mucosa. This immunomodulatory effect is complemented by the strain's antagonistic properties in reducing the presence of pathogenic Gram negative bacteria in the GIT, and decreasing the amount of LPS in the intestinal mucosa.

The compositions according to the invention that comprise an effective amount of at least one of the deposited strains, or of their mutants, can be formulated as edible, pharmaceutical or veterinary products, in which said strains are the only active agents or are mixed with one or more other active agents and/or are mixed with pharmaceutically or veterinary acceptable excipients (in the case of a pharmaceutical or veterinary product) or adequate additives (in the case of an edible product). In a particular embodiment of the invention, the products additionally contain one or more further active agents. Preferably, the additional active agent or agents are other probiotic bacteria. Depending on the formulation, the strains may be added as purified bacteria, as a bacterial culture, as part of a bacterial culture, as a bacterial culture which has been post-treated, and alone or together with suitable carriers or ingredients. Prebiotics could be also added, giving rise to s symbiotic composition. In a particular embodiment, the compositions of the invention additionally contain a prebiotic selected from the group consisting of fructooligosaccharides and galactooligosaccharides.

In another aspect, the invention provides a pharmaceutical and/or veterinary product that contains an effective amount of a composition comprising at least one of the deposited strains, or mutant strains thereof, together with adequate amounts of pharmaceutically or veterinary acceptable excipients. In this regard, the pharmaceutical product may be prepared to be administered orally in form of tablets, pills, capsules, microcapsules, granules, suspensions, syrups, freeze-dried powders, liquid preparations, etc. Selection of the excipients and the most appropriate methods for formulation in view of the particular purpose of the composition is within the scope of ordinary persons skilled in the art of pharmaceutical technology. Although oral administration is preferred, other forms are possible, such as injectable, rectal or topical.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation. Suitable carriers, excipients, etc. can be found in standard pharmaceutical texts. Likewise, the term "veterinary acceptable" means suitable for use in contact with the tissues of a non-human animal.

The strains of the invention can be also included in a variety of edible products, such as a milk products, a yogurt, a curd, a cheese (e.g. quark, cream, processed, soft and hard), a fermented milk, a milk powder, a milk based fermented product, an ice-cream, a fermented cereal based product, a milk based powder, a beverage, a dressing, and a pet food. The term "edible product" is used herein in its broadest meaning, including any type of product, in any form of presentation, which can be ingested by an animal, but excluding pharmaceutical and veterinary products. Examples of other edible products are meat products (e.g. liver paste, frankfurter and salami sausages or meat spreads), chocolate spreads, fillings (e.g. truffle, cream) and frostings, chocolate, confectionery (e.g. caramel, fondants or toffee), baked goods (cakes, pastries), sauces and soups, fruit juices and coffee whiteners. Particularly interesting edible products are dietary supplements and infant formulas. In the sense of the present invention, dietary supplements also include nutraceuticals, which are known to be extracts of foods that have a medicinal effect on human health. Fodders for animal food are also included in the scope of the invention. The compositions of the invention could be also used as an ingredient in other food products.

Accordingly, in another aspect of the invention, an edible product is provided which contains the composition of the invention together with appropriate amounts of edible ingredients. Preferably, the composition of the invention is a dietary supplement.

The effective amount of colony forming units (cfu) for each strain in the composition will be determined by the skilled in the art and will depend upon the final formulation. For instance, in edible products, the strain or strains are present in an amount from about $10^5$ cfu/g to about $10^{12}$ cfu/g, preferably in an amount from about $10^7$ cfu/g to about $10^{12}$ cfu/g, according to the current legislation. The term "colony forming unit" ("cfu") is defined as number of bacterial cells as revealed by microbiological counts on agar plates.

Dietary supplements usually contain probiotic strains in an amount ranging from $10^7$ and $10^{12}$ cfu/g. In a particular embodiment, the composition of the invention is a dietary supplement comprising between $10^9$-$10^{11}$ cfu/g, preferably around $10^{11}$ cfu/g, of the deposited strains. In another embodiment, the dietary supplement comprises $10^9$ cfu of the strain or strains of the invention.

Suitable administration regimes of the composition of the invention can be established by the person skilled in the art. The composition of the invention can be administered once a day, once a week, several days per week or several times per day. In another embodiment, the daily dose comprises $10^9$ cfu of the strain or strains of the invention.

The strains of the invention are produced by cultivating the bacteria in a suitable medium and under suitable conditions. The strains can be cultivated alone to form a pure culture, or as a mixed culture together with other microorganisms, or by cultivating bacteria of different types separately and then combining them in the desired proportions. After cultivation, the cell suspension is recovered and used as such or treated in the desired manner, for instance, by concentrating or freeze-drying, to be further employed in the preparation of pharmaceutical or edible products. Sometimes the probiotic preparation is subjected to an immobilisation or encapsulation process in order to improve the shelf life. Several techniques for immobilisation or encapsulation of bacteria are known in the art (cf. Kailasapathy et al., "Microencapsulation of Probiotic Bacteria: Technology and Potential Applications", *Curr Issues Intest Microbiol* 2002, vol. 3, p. 39-48).

If the composition according to the invention is used as a dietary supplement, it can be administered as such, can be mixed with a suitable drinkable liquid, such as water, yoghurt, milk or fruit juice, or can be mixed with solid or liquid food. In this context the dietary supplement can be in the form of tablets, pills, capsules, granules, powders, suspensions, sachets, pastilles, sweets, bars, syrups and corresponding administration forms, usually in the form of a unit dose. Preferably, the composition of the invention is administered in the form of tablets, capsules, syrups or pills, manufactured in conventional processes of preparing pharmaceutical products.

As shown in the examples below, each of the provided strains have improved characteristics when compared with commercially available *L. plantarum* strains, such as *L. plantarum* 299v or *L. plantarum* VSL#3. Particularly, the three strains posses improved hypocholesterolemic effects due to their surprisingly high BSH activity. Therefore, each of the strains can be used in the composition of the invention either on their own or in combination with the other strains of the invention. For instance, a composition of the invention can comprise an effective amount of *L. plantarum* strain CECT 7527 alone or together with pharmaceutically acceptable excipients, or edible ingredients, preservatives, etc. Also, the composition of the invention can contain an effective amount of *L. plantarum* strain CECT 7527 in combination with *L. plantarum* strain CECT 7528 and/or *L. plantarum* strain CECT 7529 together with pharmaceutically acceptable excipients, or edible ingredients, preservatives, etc.

A further aspect of the invention provides a strain of *Lactobacillus plantarum* selected from the group consisting of *Lactobacillus plantarum* CECT 7527, *Lactobacillus plantarum* CECT 7528 and *Lactobacillus plantarum* CECT 7529, or mutant strains thereof, wherein the mutant strains are obtained by using the deposited strains as starter material, and wherein the mutant strains retain or further improve the cholesterol lowering activity of the parent strains. In a particular embodiment, the strain is selected from one of the deposited strains.

The following sections describe the hypocholesterolemic capabilities of the strains of the invention, as well as their taxonomic characterization and their specific probiotic features, including their effects on the immune system. These examples are not intended to be limiting of the present invention. The results obtained demonstrate that the strains of the invention have improved probiotic features when compared with the commercial *L. plantarum* 299v strain. Further, it is shown that a composition comprising the strains of the invention has better in vivo cholesterol-lowering activity than known plant sterol-containing formulations.

Unless otherwise defined, all technical and scientific terms used herein have the same meaning as commonly understood by one of ordinary skilled in the art to which this invention belongs. Methods and materials similar or equivalent to those described herein can be used in the practice of the present invention.

Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

BRIEF DESCRIPTION OF THE DRAWINGS

FIG. 1. Pulsed field electrophoresis patterns of Sma-I (A) and Sfi-I (B) restricted genomic DNA of: 1, *Lactobacillus plantarum* 299v; 2, F2099; 3, F3147; 4, *Lactobacillus plantarum* VSL#3; 5, F3276.

EXAMPLES

1. In Vitro Hypocholesterolemic Activity of the New Strains

The strains of the present invention were isolated from infant faeces and chosen among other 500 bacterial strains for their high performance in a screening for bile salt hydrolase (BSH) activity by the method described below. The selected strains showed a clear Gram+staining, as well as bacilli morphology and were non-spore-forming. Strains were deposited under the Budapest Treaty in the Coleccion Española de Cultivos Tipo (CECT, Universidad de Valencia, Edificio de investigación, Campus de Burjassot, 46100 Burjassot, Valencia). The corresponding viability certificate was emitted and strains received the following accession numbers: *Lactobacillus plantarum* CECT 7527 (also named F2099 in this description), *Lactobacillus plantarum* CECT 7528 (also named F3147 in this description), and *Lactobacillus plantarum* CECT 7529 (also named F3276 in this description).

Date of entry in the CECT was Jul. 7, 2009 for strains F3276 and F2099, and 15 Jul. 2009 for strain F3147. Access to the deposited materials will be available during pendency of the patent application making reference to the deposits to one determined by the Director to be entitled thereto under 37 C.F.R. 1.14 and 35 U.S.C. 122. All restrictions imposed by the depositor on the availability to the public of the deposited materials will be irrevocably removed upon the granting of the pertinent U.S. patent.

Hypocholesterolemic activity of the strains was further investigated in vitro and compared to commercial control strains *L. plantarum* 299v strain (from now on Lp 299v) and *L. plantarum* strain contained in the commercial VSL#3 culture (from now on Lp VSL#3). As stated above, two mechanisms have been described for the lowering of cholesterol levels caused by lactic acid bacteria, i.e. cholesterol neosynthesis caused by the deconjugation of bile acids and through assimilation of exogenous cholesterol from the diet. Therefore, all strains were subjected to BSH activity assay and to culture cholesterol lowering test. Additionally, mixed cultures containing different combinations of the new strains were assayed to ascertain whether synergistic effects exist among the strains regarding BSH and media cholesterol lowering activities. Experimental procedures were performed as described by Hyeong-Jun Lim et al. (cf. "Isolation of cholesterol lowering lactic acid bacteria from human intestine for probiotic use", *J Vet Sci* 2004, vol. 5, p. 391-5) with slight modifications.

1.1. Bile Salt Hydrolase Activity

Strains were cultured overnight on MRS medium (pH 6.4) at 30° C. in an atmosphere containing 5% $CO_2$. After incubation, cultures were standardised to $10^8$ cfu/ml and the following mixed cultures were prepared: F2099+F3147, F2099+F3276, F3147+F3276, F2099+F3147+F3276. Mixed cultures contained the same amount of each of their constituent strains and the same total bacterial concentration as the single-strained cultures. Both single-strain cultures and mixed cultures were assayed for BSH activity. Cultures were impregnated around sterilized paper disks on MRS agar plates supplemented with 4% (w/v) sodium salt of taurodeoxycholic acid (TDCA, Sigma, USA) and 0.37 g/l $CaCl_2$. Plates were anaerobically incubated at 37° C. for 72 h, and the diameter of the precipitation zones around the disks was measured. BSH activity was then calculated by subtracting the disc diameter (DD) from the inhibition zone diameter (IZD) and dividing this difference by two following the formula GI=(IZD−DD)/2 (see TABLE 1)

TABLE 1

| Bile salt hydrolase (BSH) activity | |
|---|---|
| | BSH activity |
| F2099 | 2.10 |
| F3147 | 2.53 |
| F3276 | 3.17 |
| F2099 + F3147 | 2.63 |
| F2099 + F3276 | 3.35 |
| F3147 + F3276 | 2.90 |
| F2099 + F3147 + F3276 | 3.65 |
| Lp 299V | 1.70 |
| Lp VSL#3 | 2.00 |

These results demonstrate that the strains of the present invention have high bile salt deconjugation activity. Further, BSH activity of each of the single strains F2099, F3147 and F3276 is higher than that of the commercial strains Lp 299v and Lp VSL#3, the highest activity corresponding to strain F3276. Also, when strains are combined in a mixed culture, the BSA activity of the mixed culture is higher than that of the single-strain cultures for the same total bacterial concentration. BSH activity is particularly increased when the three strains are combined, resulting in a BSH activity that widely doubles that of Lp 299v. Thus, it appears there is a synergistic effect between the strains of the invention regarding BSH activity.

1.2. Media Cholesterol Lowering Ability

Cholesterol lowering test was performed by using soluble cholesterol MRS broth. Single-strained and mixed cultures were prepared as explained above. Soluble cholesterol (polyoxyethanylcholesterol sebacate, Sigma, USA) was filtered through 0.45 μm Millipore and supplemented into autoclaved, 0.05% L-cysteine-containing MRS broth to a final concentration of 300 mg/ml. The inoculation volume was 15 μl of bacterial culture solution as obtained above ($10^8$ cfu/ml) per 1 ml cholesterol-MRS broth, and that was anaerobically incubated at 37° C. for 24 h. Uninoculated MRS broth was also incubated at the same conditions. Following incubation, bacterial cells were removed by centrifugation and *L. plantarum* culture supernatants and uninoculated control were then assayed for their remaining cholesterol content in an automatic analyzer (Olympus AU400). The same experiment was performed in 1% w/v bile salts-containing MRS broth (bile salts from SIGMA C4951), since this last combination resembles more closely the intestinal environment. Results of these assays can be seen in TABLE 2, and are expressed as the % of cholesterol reduction with respect to uninoculated control.

TABLE 2

| Media cholesterol lowering ability by bacterial cultures. | | |
|---|---|---|
| | % Cholesterol reduction | % Cholesterol reduction (1% bile salts) |
| F2099 | 10.10 | 42.70 |
| F3147 | 9.60 | 42.70 |
| F3276 | 9.30 | 42.00 |
| F2099 + F3147 | 9.84 | 43.00 |
| F2099 + F3276 | 11.82 | 47.20 |
| F3147 + F3276 | 10.72 | 44.27 |
| F2099 + F3147 + F3276 | 13.01 | 50.85 |
| Lp 299V | 4.58 | 26.70 |
| Lp VSL#3 | 7.40 | 27.80 |

Again, the results demonstrate that the strains of the invention have better hypocholesterolemic effects as compared with the well-known commercial Lp 299v and strain Lp VSL#3. Additionally, it is shown that the cholesterol lowering effects are better when combining the three strains of the invention in a mixed culture.

2. Taxonomic Characterization of Strains

For taxonomic characterisation, the strains of the invention were grown overnight on MRS medium (pH 6.4) at 30° C. in an atmosphere containing 5% $CO_2$. Bacteria were further harvested, washed and resuspended in pre-lysis buffer (480 μl EDTA 50 mM pH 8.0; 120 μl lysozyme 10 mg/ml), and further incubated at 37° C. for 60 min. DNA was extracted using Wizard genomic DNA purification kit (Promega). After centrifugation of the pre-treated bacteria at 14000 g for 2 min to remove the supernatant, the Promega's protocol was followed. In brief, bacteria were resuspended in Nuclei Lysis Solution and incubated at 80° C. for 5 min, then cooled to room temperature. Cell lysates were incubated in RNase solution at 37° C. for 60 min and proteins were precipitated by adding the Protein Precipitation Solution and vortexing at high speed. Samples were cooled down and centrifuged at 15000 g for 3 min. The supernatants containing the DNA were transferred to clean 1.5 ml microfuge tubes and mixed with 600 μl of isopropanol by inversion. DNA was collected by centrifugation at 15000 g for 2 min and carefully pouring off the supernatant. DNA samples were washed with 600 μl of 70% ethanol by gently inverting the tube several times. Ethanol was removed by aspiration, after centrifugation at 15000 g for 2 min. Finally, the DNA pellet was resuspended in 100 μl of Rehydration Solution by incubating at 65° C. for 1 h. Samples were stored at 2-8° C.

2.1. Genus and Specie Genetic Identification

The 16S rRNA was amplified by PCR using the universal primers Eub27f and Eub1492r, which produce a fragment nearly full-sequence of 16S (more than 1000 nucleotides) (TABLE 3). Then, the DNA obtained as explained above was washed using the kit Quiaquick (Quiagene).

Four consecutive sequencing reactions were performed for each sample in a Genetic Analyzer 3130 (Applied Biosystems) using BigDye kit v. 3.1, using the primers shown in TABLE 3. Data collection and chromatograms were built using DNA Sequence Analysis v. 5.2 software (Applied Biosystems) and checked by visual analysis with Chromas (Technelysium Pty Ltd.) and BioEdit (Ibis Biosciences).

Genus Identification was carried out using the Ribosomal Database Project tool (Q. Wang et al., "Naive Bayesian Classifier for Rapid Assignment of rRNA Sequences into the New Bacterial Taxonomy", *Appl. Environ. Microbiol*, 2007, vol. 73, p. 5261-7). Species identification was performed by comparison of the obtained sequence with 16S sequences of known organisms from both RefSeq data base (www<dot>ncbi<dot>nlm<dot>nih<dot>gov</> RefSeq</>) by means of a BLASTN, and from Ribosomal Database Project (rdp<dot>cme<dot>msu<dot>edu</>, J. R. Cole et al., "The Ribosomal Database Project (RDP-II): introducing myRDP space and quality controlled public data" *Nucl. Acids Res.* 2007, vol. 35, p. 169-72). RDP tool identified the three strains F2099, F3147 and F3276 as belonging to the *Lactobacillus plantarum* species.

strains: taxonomic implications", *Int J Syst Evol Microbiol* 2005, vol. 55, p. 197-207). Lp VSL#3 and Lp 299v were also included in the assay as control strains. All strains were grown on MRS agar plates and incubated at 37° C., 5% $CO_2$ for 18 h. Cells were harvested and washed 3 times in 8 ml PET (10 mM Tris pH 7.6, 1 M NaCl), then centrifuged at 6000 rpm 10 min. Pellets were resuspended in 700 μl lysis buffer (6 mM Tris, 1 M NaCl, 0.1 M EDTA, 0.5% SLS, 0.2% deoxycholic acid; 1 mg/ml lysozyme; 40 U/ml mutanolysin; 20 (g/ml RNase). An equal volume of 1.6% low melting point agarose (FMC Bio-Products, Rockland, Me., USA) was added to the resuspended cells and solidification was allowed at 4° C. for 1 h. Inserts were transferred to 2 ml lysis buffer II (0.5 M EDTA pH 9.2, 1% N-lauryl sarcosine and 1 mg/ml pronase) and incubated at 50° C. for 48 h. Then inserts were washed at room temperature with TE buffer (10 mM Tris, 1 mM EDTA pH 8.0). Total DNA digestion was performed by Sfi-I and Sma-I restriction enzymes (Roche Diagnostics).

Pulse-field electrophoresis was carried out using CHEF DRIII apparatus (BioRad Laboratories). Inserts were loaded in a 1% agarose gel (SeaKem ME agarose, FMC BioProducts, ME, USA). TABLE 4 describes electrophoresis conditions for each enzyme. DNA MW markers were Lambda ladder PFG Marker and Low Range PFG Marker (New England Biolabs). After electrophoresis, gels were stained with ethidium bromide and UV using GelDoc System (BioRad).

TABLE 4

Electrophoresis conditions for Sfi-I and Sma-I restricted genomic DNA from F2099, F3147 and F3276 strains.

| Enzyme | Block | Initial Pulse (sec) | Final Pulse (sec) | Time (hours) |
|--------|-------|---------------------|-------------------|--------------|
| Sfi-I  | 1     | 2                   | 10                | 10           |
|        | 2     | 15                  | 25                | 6            |
| Sma-I  | 1     | 0.5                 | 5                 | 16           |

As shown in FIG. 1, pulsed field electrophoresis Sfi-I and Sma-I restriction patterns were different for F2099, F3147

TABLE 3

Primers used for amplifying and sequencing the 16S gene.

| Step | Primer | Orientation | 5' → 3' Sequence |
|------|--------|-------------|------------------|
| Amplification | Eub27f | forward | GAGTTTGATCCTGGCTCAG (SEQ ID NO: 1) |
|  | Eub1492r | reverse | TACGGYTACCTTGTTACGACTT (SEQ ID NO: 2) |
| Sequencing | 27f | forward | AGAGTTTGATCCTGGCTCAG (SEQ ID NO: 3) |
|  | 357f | forward | CGCCCGCCGCGCCCCGCGCCCGGCCCGCC GCCCCGCCCCCCTACGGGAGGCAGCAG (SEQ ID NO: 4) |
|  | 907r | reverse | CCGTCAATTCCTTTGAGTTT (SEQ ID NO: 5) |
|  | 1492r | reverse | GGTTACCTTGTTACGACTT (SEQ ID NO: 6) |

2.2. Strain Genotyping

Characterization was performed by genomic digestion and pulsed-field gel electrophoresis. F2099, F3147 and F3276 strains were subjected to a previously described protocol (A. M. Rodas et al., "Polyphasic study of wine *Lactobacillus* and F3276 strains, thus confirming that they belong to three different strains. As expected, the patterns also differed with those for the Lp 299v and Lp VSL#3 strains. In literature, it has been described that, unlike other *Lactobacillus*, *L. plantarum* species present a high genetic heterogeneity (I.

Sánchez et al., "Polyphasic study of the genetic diversity of lactobacilli associated with 'Almagro' eggplants spontaneous fermentation, based on combined numerical analysis of randomly amplified polymorphic DNA and pulsed-field gel electrophoresis patterns" *Journal of Applied Microbiology* 2004, vol. 97, p. 446-58). As shown by their PFGE, strains F2099, F3147 and F3276 look genetically very close related, so they may come from the same clone origin (F. C. Tenover et al., "Interpreting chromosomal DNA restriction patterns produced by pulsed-field gel electrophoresis: criteria for bacterial strain typing" *J Clin Microbiol* 1995, vol. 33, p. 2233-9).

3. Resistance to Gastrointestinal Environment

In order to evaluate the resistance of F2099, F3147 and F3276 strains to the transit through the GIT assays were performed in conditions mimicking the gastrointestinal environment of mammals. Thus, survival after treatment with lysozyme, oxygen peroxide, acidic environment and bile salts was quantified. Results were compared to those obtained for Lp 299v and Lp VSL#3.

3.1. Tolerance to Lysozyme:

20 μl aliquots of each bacterial strain culture grown overnight in MRS at 37° C. were placed in a 96-well plate and 200 μl medium supplemented with 100, 200 or 300 μg/ml lysozyme (Sigma) was added. Plates were incubated at 37° C., 5% $CO_2$. Bacterial growth was quantified by measuring the increase of optical density at 620 nm in an ELISA reader between 0 and 6 h incubation time. Results are expressed in % vs the control, which is the maximum growth of each of the strains in a MRS broth without lysozyme supplementation (TABLE 5).

3.2. Tolerance to Oxygen Peroxide:

20 μl aliquots of each strain culture grown overnight in MRS at 37° C. were placed in a 96-well plate. 200 μl of MRS supplemented with 10, 20 and 30 μg/ml $H_2O_2$ were added to wells and plates were incubated 30 min at 37° C. before being read at 620 nm after 0 and 6 h incubation time (TABLE 6).

3.3. Tolerance to Acidic Environment:

20 μl aliquots of each strain culture grown overnight in MRS at 37° C. were placed in a 96-well plate, then 200 μl aliquots of MRS media adjusted to different pH values with HCl were placed over bacteria containing wells. Plates were then kept at 42° C. and the increase of optical density was read in a spectrophotometer at 620 nm between 0 and 6 h. Results are expressed in % vs the control, which is the maximum growth of each of the strains in a MRS broth at pH 7.2 (TABLE 7).

3.4. Tolerance to Bile Salts:

20 μl aliquots of each bacterial strain culture grown overnight in MRS at 37° C. were placed in a 96-well plate. 200 μl supplemented with 0.3%, 0.5% and 0.1% (w/v) bile salts (SIGMA B8756-10G, 096K1213) was added to wells and adjusted to pH 3. Samples were also assayed in 200 μl of 0.3% (w/v) bile salt MRS without pH adjustment. Plates were kept at 37° C., 5% $CO_2$ and read at 0 and 6 h in a spectrophotometer at 620 nm (TABLE 8).

TABLE 5

Optical density (OD) results expressed in % of control MRS after incubation at different lysozyme concentrations

| | Lysozyme concentration (μg/ml) | | |
|---|---|---|---|
| | 100 | 200 | 300 |
| F2099 | 99.23 | 99.65 | 97.55 |
| F3147 | 96.45 | 95.72 | 93.66 |
| F3276 | 98.45 | 98.12 | 94.67 |
| Lp 299v | 92.86 | 90.02 | 85.19 |
| Lp VSL#3 | 89.23 | 87.12 | 81.19 |

TABLE 6

Optical density results expressed in % of control MRS after incubation at different $H_2O_2$ dilutions

| | $H_2O_2$ concentration (μg/ml) | | |
|---|---|---|---|
| | 10 | 20 | 30 |
| F2099 | 96.12 | 95.77 | 90.9 |
| F3147 | 98.45 | 96.80 | 94.35 |
| F3276 | 95.12 | 92.38 | 89.99 |
| Lp 299v | 95.34 | 93.24 | 87.45 |
| Lp VSL#3 | 97.12 | 90.88 | 85.45 |

TABLE 7

Optical density results expressed in % of control MRS after incubation at different pH values

| | pH | | | | | | | | |
|---|---|---|---|---|---|---|---|---|---|
| | 2 | 2.5 | 3 | 3.5 | 4 | 4.5 | 5 | 5.5 | 6 |
| F2099 | 60.45 | 62.67 | 66.58 | 70.23 | 71.89 | 77.34 | 80.24 | 85.28 | 93.45 |
| F3147 | 62.08 | 65.80 | 71.20 | 74.32 | 76.45 | 84.12 | 88.95 | 95.40 | 97.20 |
| F3276 | 58.24 | 58.23 | 60.22 | 63.56 | 64.58 | 68.34 | 74.56 | 86.34 | 92.10 |
| Lp 299v | 52.34 | 51.56 | 57.34 | 58.03 | 63.20 | 63.99 | 78.23 | 83.20 | 87.30 |
| Lp VSL#3 | 55.34 | 56.74 | 61.10 | 62.45 | 63.76 | 67.77 | 72.34 | 82.12 | 84.23 |

TABLE 8

Optical density results expressed in % of control MRS after incubation at different bile salt concentrations.

| | bile salt concentration (% w/v) | | | |
|---|---|---|---|---|
| | 0.3* | 0.3 pH 3 | 0.5 pH 3 | 1 pH 3 |
| F2099 | 117.85 | 109.34 | 103.23 | 87.12 |
| F3147 | 136.08 | 128.01 | 107.34 | 95.66 |
| F3276 | 109.80 | 104.30 | 93.67 | 72.56 |
| Lp 299v | 102.45 | 94.35 | 89.34 | 51.56 |
| Lp VSL#3 | 104.65 | 99.49 | 92.12 | 65.23 |

*No pH adjustment.

These results indicate that the strains of the invention have good viability performance when subjected to conditions that mimic the gastrointestinal environment. TABLES 5 and 6 show that the strains are resistant to high concentrations of bactericidal agents present in the mouth (lysozyme and oxygen peroxide). Strain viability is very good even at concentrations above physiological conditions (30 μg/ml lysozyme and 10 μg/ml $H_2O_2$). Regarding stomach acidic conditions, viability of the strains is also satisfactory. Further, the strains of the invention are outstandingly resistant to bile salts (see TABLE 8), even in combination with an acidic pH, as is usually the case when emptying of the stomach takes place. Altogether, the results show that the strains of this invention are viable after passage through the GIT. Moreover, the results show that the strains of the invention have a better performance than the commercial strains Lp 799v and Lp VSL#3 in the assayed conditions.

4. Adhesion to Intestine 4.1. Adhesion to Mucus

The adhesion capability of F2099, F3147 and F3276 strains was compared to that of the commercial strain Lp 299v.

Mucus was obtained by washing an intestine with PBS pH 7.4 gelatin 0.01% and proteases inhibitor (Complete®, Sigma). The mucosa was scrapped and deposited in a recipient with buffer 10 mM HEPES-Hank's salt pH 7.4 and the same inhibitors. Mucus was then washed by centrifugation at 13000 rpm for 10 min with the same buffer. The supernatants were recovered and mucus content was evaluated by Bradford protocol.

Tritium-labeled cultures were prepared as follows. 150 µl of axenic cultures of each of the microorganisms were put in MRS medium supplemented with tritium-labeled thymidine (5 µl in 3 ml of MRS) and incubated overnight at 30° C. and 5% $CO_2$. The preparations were centrifuged and pellets resuspended in PBS buffer to a concentration of $10^8$ cfu/ml. The tritium signal incorporated to the microorganisms is calculated from the initial tritium signal (the µl of tritium-labelled thymine added to the medium) and the supernatant signal. The ratio between this number (signal incorporated to the biomass) and the total number of microorganisms in the culture results in dpm/cfu (signal/bacterium).

24 h before the adhesion assay, 1 ml of the mucus solution 0.5 mg/ml was incubated in wells of ELISA plate. After washing, the $1\times10^8$ cfu/ml tritium-labelled microorganism preparations were added to the wells and incubated for 60 min at 37° C. Supernatants of each well were removed, wells washed with MEM Alpha medium (Gibco) and scrapped to release the mucus-microorganisms from the wells. Adhesion of the strains is calculated by counting tritium signal in a scintillation reader (Wallac 1410) of the mucus-microorganism preparation in the wells and dividing by the dpm/cfu as obtained above. The result is the number of bacteria adhered per unit of mucus area. $6.80\times10^5$, $6.58\times10^6$ and $7.31\times10^6$ cfu of the strains F2099, F3147 and F3276, respectively, can bind to 2 $cm^2$ of intestinal mucus. Comparing with the Lp 299v commercial strain, the strains of the present invention have a much better adhesion capability.

4.2. Adhesion to Caco-2 Cells

Caco-2 ECACC N°: 86010202 cells were obtained from American Type Culture Collection (ATCC). The experimental procedure to obtain the number of bacteria that adhere per unit of caco-2 cells area is essentially the same as explained above for adhesion to mucus. The results may showed that $3.12\times10^6$, $2.11\times10^6$ and $5.19\times10^5$ cfu of the strains F2099, F3147 and F3276, respectively, can bind to 2 $cm^2$ of caco-2 cells. Once again, compared to the commercial strain Lp 299v, the strains of the invention have better adhesion capability.

5. Toxicity Assays

A pre-fixed mixed culture of F2099, F3147 and F3276 strains (this mixed culture will be called from now on AB-LIFE) was administered at $5\times10^{10}$ cfu/kg in PBS to six 9-weeks old Wistar rats (male and female) over two consecutive days to a total dose of $10^{11}$ cfu/kg. Animals were fed with fodder (Teklacd 2014) and water ad libitum. Administration was after eating over a full stomach and aided by an orogastric tube. The same feeding regime was applied to 6 control rats, who received PBS alone. Every two days, animal wellbeing was determined by assigning values to parameters such as weight, behaviour and response to stimuli. Total score results from the sum of the values obtained in each parameter: weight+behaviour+response to stimuli. Altogether, no negative effects on animal well-being were noted during the study.

Animals were sacrificed on day 7 by $CO_2$ inhalation. A full necropsy was performed in order to find macroscopic organ damage. Samples of mesenteric lymph nodes and liver were taken to assay for bacterial translocation. Approximately 5 mg of each sample was homogenized in 1 ml 0.01% gelatin PBS. 100 µl from this homogenate were plated either on McConkey plates or MRS plates. Colonies were counted after incubation at 37° C. for 48 h. Results are displayed in TABLE 9 and TABLE 10. There were a few LAB colonies observed in MRS plates from control and AB-LIFE-fed animals which correspond to a normal basal translocation of LAB (J. S. Zhou et al., "Acute oral toxicity and bacterial translocation studies on potentially probiotic strains of lactic acid bacteria", *Food Chem Toxicol* 2000, vol. 38, p. 153-61).

In conclusion, the results show that oral administration of AB-LIFE culture is safe since it does not lead to an increase in translocation of LAB nor do they facilitate enterobacterial translocation. All the animals showed a similar body weight evolution along the study. No significant differences were observed in the fodder and water consumption. Neither clinical symptom nor alteration of the animals' wellbeing was detected. No macroscopic damages in organs and cavities were detected during the histopathological examination.

TABLE 9

Bacterial translocation to the liver of AB-LIFE-fed animals.

| Group | Sex | Enterobacteria (cfu/mg) | Lactic acid Bacteria (cfu/mg) | Maximum observed Translocation (cfu/mg) |
|---|---|---|---|---|
| Control | Males | 0/3 | 0/3 | 0 |
|  | Females | 0/3 | 0/3 | 0 |
| AB-LIFE | Males | 0/3 | 1/3 | 1 |
|  | Females | 0/3 | 0/3 | 0 |

Numbers indicate the number of animals with positive bacterial growth and the maximal number of cfu/mg of tissue.

TABLE 10

Bacterial translocation to the mesenteric lymph nodes of AB-LIFE-fed animals.

| Group | Sex | Enterobacteria (cfu/mg) | Lactic acid Bacteria (cfu/mg) | Maximum observed Translocation (cfu/mg) |
|---|---|---|---|---|
| Control | Males | 0/3 | 1/3 | 1 |
|  | Females | 0/3 | 1/3 | 1 |
| AB-LIFE | Males | 0/3 | 1/3 | 1 |
|  | Females | 0/3 | 1/3 | 1 |

Numbers indicate the number of animals with positive bacterial growth and the maximal number of cfu/mg of tissue.

6. Antagonistic Properties

In order to assess whether strains F2099, F3147 and F3276 presented antagonistic activities, a Campbell protocol was performed using agar plates seeded with bacterial pathogens in Oxoid medium. Pathogens used in this study were selected among those commonly present in the human gastrointestinal tract (see TABLE 11). Plates were swabbed uniformly and grown to confluence at the appropriate temperatures in a 5% $CO_2$ incubator. Then, a cylinder section of a uniformly seeded, confluent F2099, F3147 or F3276 agar plate was placed loan-to-loan over the pathogen plate and incubated overnight at 37° C.

Next day, inhibition zones were measured by placing the agar plate over a flat rule. Growth inhibitory activity was then calculated by subtracting the cylinder diameter (CD) from the inhibition zone diameter (IZD) and dividing this difference by two following the formula GI=(IZD−CD)/2. The inhibiting capabilities of the strains of this invention were compared to that of the commercial strains Lp299v and Lp VSL#3.

TABLE 11

Growth inhibition values according to the formula depicted above.

|  | F2099 | F3147 | F3276 | Lp VSL#3 | Lp 299v |
|---|---|---|---|---|---|
| *Salmonella enterica* Enteritidis CECT 4155 | 0.45 | 0.775 | 0.6 | 0.6 | 0.25 |
| *Salmonella enterica* Typhimurium CECT 4594 | 0.6 | 0.6 | 0.6 | 0.55 | 0.15 |
| *Escherichia coli* isolated from infant faeces | 0.35 | 0.7 | 0.675 | 0.45 | 0.2 |
| *Proteus mirabilis* CECT 484 | 0.975 | 0.85 | 0.675 | 0 | 0 |
| *Klebsiella oxytoca* K108 CIP 103434 | 0.7 | 0.85 | 0.75 | 0.9 | 0.15 |
| *Pseudomonas aureginosa* isolated from infant faeces | 0.3 | 0.3 | 0.2 | 0.2 | 0 |
| *Yersinia pseudotuberculosis* CIP 104896 | 1 | 3 | 10.25 | 1.8 | 0.4 |
| *Clostridium perfringens* isolated from infant faeces | 0 | 0 | 1.7 | 0.15 | 0 |
| *Clostridium ramnosum* ATCC 13937 | 0 | 0 | 0.3625 | 0.2 | 0 |
| *Enterococcus faecalis* CIP A186 | 0.625 | 0.8 | 0.7 | 0.45 | 0 |

F2099, F3147 and F3276 strains inhibited growth of most of the pathogenic strains shown in TABLE 11. Thus, they benefit the intestinal microbiota balance due to their capacity to inhibit the growth of pathogenic strains. The strains of this invention had generally better antagonistic properties when compared to the commercial control strains.

7. In Vitro Evaluation of the Immunomodulation Ability of Cytokine Production in an Intestinal Mucosa Model.

The selected mucosal model is the monocyte cell line THP-1, due to its sensitivity to bacterial components like LPS (as inductor of the inflammatory response), and its susceptibility to modulate its cytokine production when there are molecules in the medium suitable for the induction of the production of an anti-inflammatory cytokine pattern.

THP-1 cells obtained from the ATCC were grown in DMEM medium in 24-wells ELISA plates to a final concentration of $10^6$ monocytes/well, approximately. The cells were stimulated with 10 ng/ml LPS during 2.5 hours before adding the bacterial strains. F2099, F3147, F3276 and Lp 299v strains were previously grown over night in MRS medium at 37° C. in a 5% $CO_2$ atmosphere. After the incubation, microorganism concentration was calculated using the Neubauer-counting chamber and properly diluted to obtain a final ratio of 25:1 ($2.5 \times 10^7$) cfu/monocytes in 500 μl of DMEM in the ELISA-wells with THP-1 cells. Each dilution is generated with DMEM medium supplemented with gentamicin (50 μg/ml), ampicillin (10 μg/ml) and chloranfenicol (12 μg/ml).

Co-incubation of THP-1 cells with *L. plantarum* strains was 24 hours, with aliquots being taken for further analysis at 6 hours and at the end of the experiment. Aliquots were centrifuged and the supernatants assayed for TNF-α and IL-10 by flow cytometry by using the commercial Kit Human Soluble Protein Master Buffer (BD Cytometric Bead Array) following manufacturer instructions.

For the interpretation of the obtained results, the slope between the obtained values at 6 and 24 hours was obtained and normalised. Normalized slope is calculated with the following formula which is provided by the manufacturer:

$$NS = ((1\text{-IL value 24 h/IL value 6 h})/24) \times 100;$$

wherein NS is the normalized slope, and IL (or TNF-α) value is the concentration of the IL-10 or TNF-α at 6 or 24 hours. Results are expressed in pg/ml.

The reason for selecting this method is to obtain a standard value that allows a transversal comparison between the experiments (TABLE 12), since the evolution of cytokines concentration is more interesting than their absolute value (pg/ml). In the values obtained at 6 hours, THP-1 cells are still under induction of LPS; later, the concentration of TNF-α is elevated and the IL-10 reduced. At 24 hours it is possible to observe the reversion of the cytokine production profile (reduction of TNF-α and the increase of IL-10).

TABLE 12

Normalised slopes showing induction (positive slope) or inhibition (negative slope) of IL-10 and TNF-α in LPS-induced THP-1 cells.

|  | IL-10 | TNF-α |
|---|---|---|
| F2099 | 20.56 | −1.23 |
| F3147 | 37.56 | −1.61 |
| F3276 | 31.46 | −2.34 |
| Lp 299v | 21.42 | −0.52 |

As shown in TABLE 12, LPS-induced THP-1 cells induce the production of IL-10 in the presence of *L. plantarum* strains, IL-10 induction being specially high in the presence of the strain F3276. Additionally, F2099, F3147 and F3276 have a higher inhibition activity on inflammatory TNF-α production when compared to commercial Lp 299v.

8. Short Chain Fatty Acid Production

For assaying propionic and butyric acid production, the strains of the invention and control strains were grown on basal medium supplemented with 1% w/v of each of the following fibers: inulin (SIGMA I2255), pectin (SIGMA 76282) and fructooligosaccharides (FOS) (SIGMA F8052), which are fibres commonly present in the daily diet. Composition of the basal medium can be seen in TABLE 13. The medium was preincubated during 12 hours in anaerobic atmosphere. After inoculation with each of the Lp strains, the media were incubated overnight at 37° C. in anaerobic conditions. Overnight cultures were then centrifuged and the supernatant quickly liquid nitrogen freezed for subsequent HPLC analysis in an Agilent 1100 chromatograph using a Tracer Extrasil ODS2 (3 μm, 15×0.4 cm) reverse phase column. Results for propionic and butyric acid concentrations in the samples can be seen in TABLE 14.

TABLE 13

Composition of basal medium.

| Compound | Concentration |
|---|---|
| Peptone | 2 g/L |
| Yeast extract | 2 g/L |
| NaCl | 0.1 g/L |
| $K_2HPO_4$ | 0.04 g/L |
| $KH_2PO_4$ | 0.04 g/L |
| $MgSO_4\,7H_2O$ | 0.01 g/L |
| $CaCl_2\,6H_2O$ | 0.01 g/L |
| $NaHCO_3$ | 2 g/L |
| Hemin | 0.05 g/L |

TABLE 13-continued

Composition of basal medium.

| Compound | Concentration |
|---|---|
| HCl Cysteine | 0.5 g/L |
| Bile Salt | 0.5 g/L |
| Tween 80 | 2 g/L |
| Vitamin K1 | 10 μl |

TABLE 14

Propionic and butyric acid production from *L. plantarum* strains grown on inulin, pectin and FOS-containing basal medium.

| | Propionic acid (mg/ml) | Butyric acid (mg/ml) |
|---|---|---|
| F2099 | 15.546 | 14.185 |
| F3147 | 12.23 | 12.294 |
| F3276 | 44.939 | 21.636 |
| Lp 299v | 12.898 | 9.195 |

From the results above it can be concluded that the strains of this invention produce large quantities of propionic and butyric acids, thus exercising beneficial effects to the host organism.

9. In Vivo Hypocholesterolemic Activity

The cholesterol-lowering effect of a probiotic composition of the invention in hypercholesterolemic subjects was investigated in a randomised, double-blind, placebo-controlled, parallel clinical trial. The study additionally contemplated further cardiovascular-related parameters, as well as the tolerability of the probiotic composition and its organoleptic properties.

60 Hypercholesterolemic subjects aged between 18 and 65 years participated in the study. Participant's body mass index (BMI) was between 19 and 30 Kg/m$^2$, total serum cholesterol (total-C) between 200 and 300 mg/dl and low density cholesterol (LDL-C) between 130 and 190, except for subjects presenting two or more cardiovascular risk factors, for which LDL-C was comprised between 100 and 190 mg/dl. None of the participants had received any kind of hypocholesterolemic treatment during the four weeks preceding the study. Subjects with hypertriglyceridemia higher than 350 mg/dl or having suffered a cardiovascular isquemic episode within the 6 months to the beginning of the study were excluded. Pregnant or breast-feeding women and subjects allergic to any of the components of the compositions were also excluded. The difference between male and female participants was not higher than 20%. All participants provided a written informed consent to participate and the study protocol was reviewed and approved by an independent ethical committee.

During 12 weeks participants received one sole oral daily dose of either control composition (placebo) or probiotic composition comprising $1.2*10^9$ cfu of a mixed culture of equal proportions of the three strains of the invention F2099, F3147 and F3276 (AB-LIFE 2). The formulation of placebo and AB-LIFE compositions can be seen in table 15. Both compositions were administered in the form of a plant gelatine capsule. Subject's LDL-C, total-C, LDL/HDL, LDL-oxidised, triglycerides, arterial tension, basal glycemia, weight, waist/hips index, body fat and well-being were monitored throughout the study. Further, the organoleptic properties and tolerability of the compositions were evaluated. Measured values for both AB-LIFE 2 probiotic group and placebo group were statistically analysed using SPSS program.

TABLE 15

Formulation of probiotic AB-LIFE 2 and placebo compositions (values in mg per capsule).

| AB-LIFE 2 | Placebo |
|---|---|
| F2099, F3147 and F3276: 100 | Corn starch: 100 mg |
| Microcrystaline cellulose (pH 10.2): 71.1 | Microcrystaline cellulose (pH 10.2): 71.1 |
| Talc: 2.6 | Talc: 2.6 |
| Magnesium stearate: 1.3 | Magnesium stearate: 1.3 |

Results of the clinical trial are shown in Tables 16 and 17. Mean values and standard deviations for total-C, LDL-C and LDL-oxidised before and after the treatment for both placebo and probiotic groups can be observed in table 16. Percentage of reduction and intra-group statistical analysis are shown in TABLE 17. It is therefore concluded that AB-LIFE 2 is an effective hypocholesterolemic agent. Moreover, when compared with products of similar indication, like plant sterol, the total-C reduction exerted by AB-LIFE 2 consumption is higher (Plana N. et al., "Plant sterol-enriched fermented milk enhances the attainment of LDL-cholesterol goal in hypercholesterolemic subjects", Eur J Nutr., 2008, vol. 47, p. 32-39).

TABLE 16

Mean values and standard deviations for total-C, LDL-C and LDL-oxidised.

| | total-C_t0 | | total-C_tf | |
|---|---|---|---|---|
| | Mean | Std. Devia | Mean | Std. Devia |
| Placebo | 252.63 | 23.47 | 242 | 22.676 |
| AB-LIFE | 247.43 | 31.28 | 213.77 | 18.68 |

| | LDL-C_t0 | | LDL-C_tf | |
|---|---|---|---|---|
| | Mean | Std. Devia | Mean | Std. Devia |
| Placebo | 168.4 | 19.592 | 158.53 | 18.17 |
| AB-LIFE | 166.67 | 21.595 | 142.17 | 13.28 |

| | LDLoxidised_t0 | | LDLoxidised_tf | |
|---|---|---|---|---|
| | Mean | Std. Devia | Mean | Std. Devia |
| Placebo | 56.42 | 9.99 | 55.38 | 9.71 |
| AB-LIFE | 54.68 | 10.99 | 47.23 | 8.32 | t0, baseline values; tf, values at the end of the 12 week treatment.

TABLE 17

Percentage of reduction (and intra-group statistical analysis) of total-C, LDL-C and LDL-oxidised in the probiotic AB_LIFE group.

| Total-C | 13.60% (p < 0.05) |
|---|---|
| LDL-C | 14.30% (p < 0.05) |
| LDL-oxidised | 13.62% (p < 0.05) |

REFERENCES CITED IN THE APPLICATION

Tanaka H, Doesburg K, Iwasaki T, Mierau I, "Screening of Lactic Acid Bacteria for Bile Salt Hydrolase Activity". *Journal of Dairy Science* 1999, vol. 82, p. 2530-35.

Bukowska H, Pieczul-Mróz J, Jastrzebska M, Chetstowski K, Naruszewicz M, "Decrease in fibrinogen and LDL-cholesterol levels upon supplementation of diet with *Lactobacillus plantarum* in subjects with moderately elevated cholesterol". *Atherosclerosis* 1998, vol. 137, p. 437-38.

Wong J M, de Souza R, Kendall C W, Emam A, Jenkins D J, "Colonic health: fermentation and short chain fatty acids". *J Clin Gastroenterol* 2006, vol. 40, p. 235-43.

Naruszewicz M, Kortowska-Wojciechowska M, "Potential parapharmaceuticals in the traditional Polish diet". *Journal of Physiology and Pharmacology* 2005, vol. 56, suppl 1, p. 69-78.

Goldstein M, Mascitelli L, Pezzetta F, "Statins, plant sterol absorption, and increased coronary risk". *Journal of Clinical Lipidology,* 2008, vol. 2, p. 304-305.

Kailasapathy K, "Microencapsulation of Probiotic Bacteria: Technology and Potential Applications". *Curr Issues Intest Microbiol* 2002, vol. 3, p. 39-48.

Lim H J, Kim S Y, Lee W K, "Isolation of cholesterol lowering lactic acid bacteria from human intestine for probiotic use". *J Vet Sci* 2004, vol. 5, p. 391-5.

Wang Q, Garrity G M, Tiedje J M, Cole J R, "Naive Bayesian Classifier for Rapid Assignment of rRNA Sequences into the New Bacterial Taxonomy". *Appl. Environ. Microbiol* 2007, vol. 73, p. 5261-7.

RefSeq data base, http://www.ncbi.nlm.nih.gov/RefSeq/ Ribosomal Database Project, http://rdp.cme.msu.edu/

Cole J R, Chai B, Farris R J, Wang Q, Kulam-Syed-Mohideen A S, McGarrell D M, Bandela A M, Cardenas E, Garrity G M, Tiedje J M, "The Ribosomal Database Project (RDP-II): introducing myRDP space and quality controlled public data" *Nucl. Acids Res.* 2007, vol. 35, p. 169-72.

Rodas A M, Ferrer S, Pardo I, "Polyphasic study of wine *Lactobacillus* strains: taxonomic implications", *Int J Syst Evol Microbiol* 2005, vol. 55, p. 197-207.

Sánchez I, Seseña S, Palop L L, "Polyphasic study of the genetic diversity of lactobacilli associated with 'Almagro' eggplants spontaneous fermentation, based on combined numerical analysis of randomly amplified polymorphic DNA and pulsed-field gel electrophoresis patterns", *Journal of Applied Microbiology* 2004, vol. 97, p. 446-58.

Tenover F C, Arbeit R D, Goering R V, Mickelsen P A, Murray B E, Persing D H, Swaminathan B, "Interpreting chromosomal DNA restriction patterns produced by pulsed-field gel electrophoresis: criteria for bacterial strain typing" *J Clin Microbiol* 1995, vol. 33, p. 2233-9.

Zhou J S, Shu Q, Rutherfurd K J, Prasad J, Gopal P K, Gill H S, "Acute oral toxicity and bacterial translocation studies on potentially probiotic strains of lactic acid bacteria", *Food Chem Toxicol* 2000, vol. 38, p. 153-61.

Plana N, Nicolle C, Ferre R, Camps J, Cos R, Villoria J, Masana L; DANACOL group, "Plant sterol-enriched fermented milk enhances the attainment of LDL-cholesterol goal in hypercholesterolemic subjects", *Eur J Nutr.,* 2008, vol. 47, p. 32-39.

---

The invention claimed is:

1. A composition comprising an effective amount of at least one of the strains selected from the group consisting of *Lactobacillus plantarum* CECT 7527, *Lactobacillus plantarum* CECT 7528, *Lactobacillus plantarum* CECT 7529, and mutant strains thereof, wherein the mutant strains are obtained by using the deposited strains as starter material, and wherein the mutant strains retain or further improve the cholesterol lowering activity of the parent strains.

2. The composition according to claim 1, which comprises an effective amount of the strains *Lactobacillus plantarum* CECT 7527, *Lactobacillus plantarum* CECT 7528, and *Lactobacillus plantarum* CECT 7529.

3. A pharmaceutical and/or veterinary product comprising an effective amount of the composition of claim 1, together with appropriate amounts of pharmaceutically or veterinary acceptable excipients.

4. An edible product comprising an effective amount of the composition of claim 1, together with appropriate amounts of other edible ingredients.

5. The edible product according to claim 4, which is a dietary supplement.

6. The edible product according to claim 5, which is a nutraceutical.

7. The edible product according to claim 4, which is in the form of a tablet, capsule, syrup or pill.

8. The edible product according to claim 4, which is a dairy product or a meat product.

9. A strain of *Lactobacillus plantarum* selected from the group consisting of *Lactobacillus plantarum* CECT 7527, *Lactobacillus plantarum* CECT 7528 and *Lactobacillus plantarum* CECT 7529.

10. The composition according to claim 1, which comprises an effective amount of at least one of the strains selected from the group consisting of *Lactobacillus plantarum* CECT 7527, *Lactobacillus plantarum* CECT 7528, and *Lactobacillus plantarum* CECT 7529.

11. A method for the prevention and/or treatment of cardiovascular disorders in an animal, including a human, comprising:
   administering to said animal in need thereof the composition of claim 1.

12. The method according to claim 11, which comprises administering an effective amount of the composition in combination with statins.

13. The method according to claim 11, wherein the animal, including human, is sterol hyperabsorbent.

14. A method for reducing cholesterol in an animal, including a human, comprising:
   administering to said animal in need thereof the composition of claim 1.

15. The method according to claim 14, which comprises administering an effective amount of the composition in combination with statins.

16. The method according to claim 14, wherein the animal, including human, is sterol hyperabsorbent.

* * * * *